United States Patent [19]

Akao et al.

[11] Patent Number: 4,709,487
[45] Date of Patent: Dec. 1, 1987

[54] METHOD FOR PROCESSING BY HEATING AND EQUIPMENT FOR SAME

[75] Inventors: Takeshi Akao; Toshio Furukawa, both of Chiba, Japan

[73] Assignee: Kikkoman Corporation, Chiba, Japan

[21] Appl. No.: 834,928

[22] Filed: Feb. 28, 1986

[30] Foreign Application Priority Data

Feb. 28, 1985 [JP] Japan ................. 60-39698

[51] Int. Cl.⁴ .............................. F26B 3/10
[52] U.S. Cl. ......................... 34/10; 34/15; 34/33; 34/34; 34/39; 34/57 R; 34/57 E
[58] Field of Search ............. 34/10, 57 R, 57 E, 86, 34/92, 191, 15, 33, 34, 39; 406/160, 161, 176, 183, 192

[56] References Cited

U.S. PATENT DOCUMENTS 3,068,584 12/1962 Schaub et al. ............ 34/57 E
3,754,926 8/1973 Strommer et al. .
3,955,486 5/1976 Strommer .

FOREIGN PATENT DOCUMENTS 0094448 6/1986 European Pat. Off. .

| | | |
|---|---|---|
| 45-8927 | 3/1970 | Japan . |
| 46-34747 | 10/1971 | Japan . |
| 54-23971 | 8/1979 | Japan . |
| 55-24865 | 7/1980 | Japan . |
| 58-42743 | 9/1983 | Japan . |

*Primary Examiner*—Larry I. Schwartz
*Attorney, Agent, or Firm*—Bogucki, Scherlacher, Mok & Roth

[57] ABSTRACT

In a method for processing by heating a powder-like and/or granular substance including steps of charging the powder-like and/or granular substance as a matter to be processed into a heated and pressurized direct-heating medium stream, heating to process while transferring the powder-like and/or granular substance in a heating tube (4), and thereafter discharging the powder-like and/or granular substances from the heating tube (4), the direct-heating medium stream is forced to whirl for heating to process while spirally transferring the powder-like and/or granular substance in the heating tube (4). The powder-like and/or granular substance as heated to be processed is discharged out of the heating tube (4), through a discharge mechanism (5) adapted to control the pressure in the heating tube (4).

17 Claims, 18 Drawing Figures

METHOD FOR PROCESSING BY HEATING AND EQUIPMENT FOR SAME

BACKGROUND OF THE INVENTION

1. Field of the Invention

The present invention generally relates to a method for processing by heating, as well as an equipment for same. More particularly, the invention relates to a method for processing by heating a variety of powder-like and/or granular substances such as materials of medicines, cosmetics, or foods, or grains, as well as an equipment for same.

2. Description of Relevant Art

The present applicant has already proposed, by Japanese Patent Publication No. 46-34747 (published on Oct. 12, 1971), "a method for producing swollen foods by a heating method of a flash system and an equipment for same", in which a heating process of grain is performed by use of superheated steam.

In such conventional art, there was employed a system in which a substance to be processed was heated by only the heat of a hot gas adapted for flashing to transport the substance, so that the quantity of gas for transportation was required to be much in comparison with that needed in ordinary cases of air transportation. Exemplarily, in cases of air transportation without heating, the mixing ratio of the quantity of a substance or substances to be transported to that of a transportation gas or transportation gases was found within a range of 2 to 10, whereas in conventional art of such system as described such ratio was approximately within 0.5 to 0.7.

In such conventional art, therefore, associated individual equipments such as a superheater, a heating tube, and a cyclone were enlarged in size, thus becoming high in cost, while enlarging the size of a process line as well, which was disadvantageous also in view of available space, and besides, in cases where a hot gas or hot gases was or were recirculated, there was resulted the enlargement in size of a blower, thus raising the cost of power as well.

Although, in addition to such conventional art, there can be enumerated, as conventional art in which a substance to be processed was heated to be processed by flashing with a hot gas, other examples such as "a texturing method of proteinic substances" in Japanese Patent Publication No. 54-23971 (published on Aug. 17, 1979), "an equipment for the texturing of proteins" in Japanese Patent Publication No. 55-24865 (published on July 2, 1980), and "a method for processing foods and an equipment for same" in Japanese Patent Publication No. 58-42743 (published on Sept. 21, 1983), these methods and equipments, in which also a hot transportation gas was the heat source in any case, fundamentally had similar problems to such conventional art as first described.

Further, the present applicant has already proposed, in Japanese Patent Application No. 55-158869 (filed on Nov. 13, 1980), an art in which an annular layer of a substance to be processed was formed on the inner wall of a pressure vessel before heating to process the substance, whereas also such conventional art, in which such substance was made in the form of an annular layer with a stirring machine, had shortcomings such as due to breakage of the substance to be processed and/or that the efficiency of heat exchange was not very high.

The present invention has been achieved, in view of such problems in conventional methods for processing by heating as well as in conventional equipments for same, to effectively solve these problems.

SUMMARY OF THE INVENTION

Accordingly, an object of the present invention is to provide a method for processing by heating and an equipment for same, which permit, with a heating medium such as superheated steam, the sterilization by heating of a powder-like and/or granular substance or, in cases where this substance is such as of a grain or of a food, the denaturalization by heating thereof to be effected in an efficient manner, while aiming at rendering small in size the entirety of equipment.

To achieve the object, the present invention provides a method for processing by heating a powder-like and/or granular substance comprising a step of charging the powder-like and/or granular substance as a matter to be processed into a heated and pressurized medium stream adapted for directly heating, a step of heating to process while transferring the powder-like and/or granular substance in a heating tube by the direct-heating medium stream, and a step of discharging from the heating tube the powder-like and/or granular substance as it is heated to be processed by the direct-heating medium stream, wherein the direct-heating medium stream is made to whirl in the heating tube, to spirally transfer the powder-like and/or granular substance.

Moreover, the present invention provides a method for processing by heating a powder-like and/or granular substance comprising a step of charging the powder-like and/or granular substance as a matter to be processed into a heated and pressurized medium stream adapted for directly heating, a step of heating to process while transferring the powder-like and/or granular substance in a heating tube by the direct-heating medium stream, and a step of discharging from the heating tube, through a discharging means, the powder-like and/or granular substance as it is heated to be processed by the direct-heating medium stream, wherein the direct-heating medium stream is made to whirl to spirally transfer the powder-like and/or granular substance in the heating tube, and the discharging means is adapted to control the pressure in the heating tube.

Further, the present invention provides an equipment for processing by heating a powder-like and/or granular substance comprising a heating tube, a means for charging the powder-like and/or granular substance as a matter to be processed into the heating tube, a heating medium stream supply means for supplying a medium stream adapted for directly heating the powder-like and/or granular substance and for transferring the powder-like and/or granular substance in the heating tube, and a whirling stream generation means for making the medium stream whirl to spirally transfer the powder-like and/or granular substance in the heating tube.

Still more, the present invention provides an equipment for processing by heating comprising a heating tube, a means for charging a powder-like and/or granular substance as a matter to be processed into the heating tube, a heating medium stream supply means for supplying a medium stream adapted for directly heating the powder-like and/or granular substance and for transferring the powder-like and/or granular substance in the heating tube, a whirling stream generation means for making the medium stream whirl to spirally transfer the powder-like and/or granular substance in the heating tube, and a discharging means for discharging from the heating tube the powder-like and/or granular substance as it is heated to be processed by the medium stream, the discharging means being adapted to control the pressure in the heating tube.

The above and further features, objects and advantages of the present invention will more fully appear from the following detailed description of a preferred embodiment of the invention, when the same is read in conjunction with the accompanying drawings, including a number of modifications of the embodiment and modified examples of a part thereof.

DETAILED DESCRIPTION OF THE PREFERRED EMBODIMENT

Figure 1:
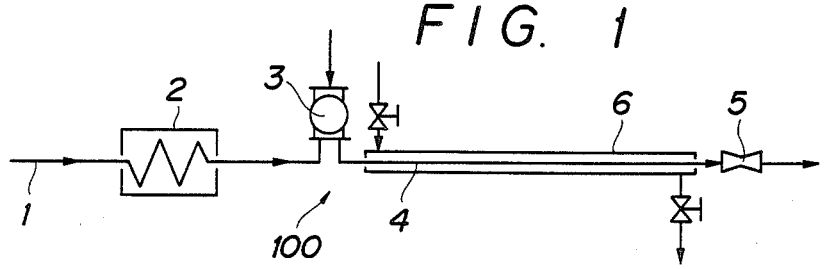
FIG. 1 is a flow diagram schematically showing the basic constitution of an equipment for processing by heating according to a preferred embodiment of the present invention, in which a direct-heating medium is let to run in a one-pass manner.

FIG. 1 is a schematic diagram of a heating process equipment 100 as a preferred embodiment for execution of the present invention. Pressurized steam, saturated steam for example, is supplied from a boiler (not shown) and lead along a supply line 1 to a heater 2 as a superheater, where it is heated to obtain superheated steam as a direct-heating medium in this embodiment. The line 1 is connected downstream of the heater 2 to a rotary valve 3 as a means for charging a powder-like and/or granular substance as a material, which valve 3 is connected downstream thereof to a heating tube 4 as a whirling stream generating tube employed for heating purpose, which tube 4 in turn is connected downstream thereof to a restriction tube or nozzle 5 as a pressure control mechanism concurrently functioning as a discharge means, from which the material as processed is taken out as a product and the heating medium is wasted. Around the heating tube 4 is provided a jacket 6 as an indirect-heating mechanism, through which an indirect-heating medium such as saturated steam or hot water is conducted.

The material charged from the rotary valve 3 is carried with streams of the superheated steam as a direct-heating medium adapted for transfer, and transferred from downstream of the line 1 into the heating tube 4, where, being transported with streams of the hot medium, it is forced to swirl, thus spirally moving like vortices, so that the material is thoroughly exposed to and uniformly heated by the heating medium. Moreover, since the heating tube 4 itself is heated from outside with the indirect-heating medium in the jacket 6, the material moving as swirling streams in the tube 4 is additionally or indirectly heated, when flowing along the tube wall, thus assuring efficient heating. Still more, by streams of the medium as a transportation carrier heated to be hot, there is effected the sterilization as well as thermal denaturalization of the material. Incidentally, such flow in the heating tube 4 has a pressure thereof controlled to establish given requirements of the heating process, with the restriction tube 5 or nozzle installed downstream of the tube 4.

Figure 2:
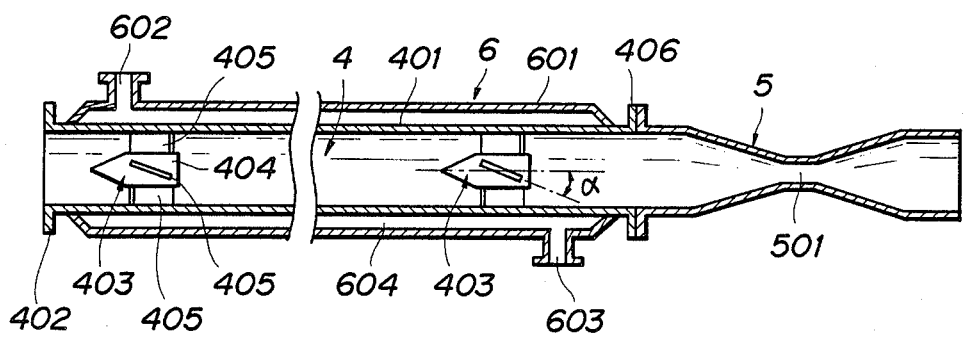
FIG. 2 is a sectional view showing a heating tube and a restriction tube as a nozzle in the equipment of FIG. 1.

FIG. 2 is a longitudinal sectional view for showing the constitution of the heating tube 4 as a whirling stream generating tube. The tube 4 consists of a tube body 401 connected upstream thereof through a flanged part 402 to the line 1, and has disposed therein a plurality of whirling stream generating stationary blade assemblies as swirlers 403, two thereof being shown: one in the upstream part, which swirler 403 comprises a boss portion 404 and a quadruple of radial fins 405 equi-angularly spaced apart to be fixed on the boss portion 404, each fin 405 being inclined to have a skew angle $\alpha$ with respect to the longitudinal direction of the tube 4. Like swirler 403 is shown also in the downstream part of the tube body 401. Those swirlers 403 are secured to the tube body 401 by fixing respective arcuate outer circumferences of fins 405 thereof to the inner circumference of the tube body 401, whereas they may be arbitrary in the number and voluntary in the interval therebetween. The tube body 401 is connected downstream thereof through another flanged part 406 to the restriction tube 5, which is provided with a restriction 501 and adapted for controlling the inner pressure of the tube body 401 by varying the inside diameter of the restriction 501, as well as for discharging the material as heated to be processed.

Around the outer circumference of the tube body 401 as an inner tube, the indirect-heating mechanism is provided as an outer tube 601 surrounding the inner tube 401, which tube 601 is closed at both upstream and downstream ends of the inner tube 401 and has formed at the upstream end an inlet 602 of the indirect-heating medium and at the downstream end an outlet 603 of same. Between the respective bodies of the inner and outer tubes 401, 601 is defined a path 604 for conduction therethrough such as of saturated steam or hot water.

In this embodiment with such constitution as described, therefore, saturated steam for example, as it is generated at the boiler, is supplied through the superheater 2, where it becomes superheated steam, and enters via the rotary valve 3 into the heating tube 4, while the material is put on streams of the superheated steam, when the steam is passing the valve 3, and charged therewith into the tube 4 as a swirling stream generating tube adapted for heating as described. In the heating tube 4, the material is whirled to be well-mixed with and, concurrently, directly heated under pressure by the superheated steam, while, in addition thereto, being indirectly heated by the medium in the path 604. Then, through the restriction tube 5, the material as processed is discharged under atmospheric pressure.

Figure 3:
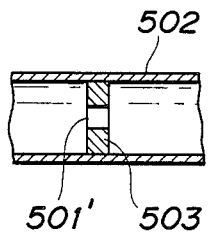
FIG. 3 is a view showing a first modified example of the restriction tube.

FIG. 3 is a sectional view showing a partially modified example of the restriction tube 5 of the foregoing embodiment of the invention. Although in the embodiment the tube 5 is reduced at a longitudinally intermediate part of the tube body itself, in the modified example a restriction tube 502, which is uniform in inside diameter along the length, has fixed therein such a member 503 that is formed with an orifice 501' at the central part thereof.

Around the outer circumference of the tube body 401 as an inner tube, the indirect-heating mechanism is provided as an outer tube 601 surrounding the inner tube 401, which tube 601 is closed at both upstream and downstream ends of the inner tube 401 and has formed at the upstream end an inlet 602 of the indirect-heating medium and at the downstream end an outlet 603 of same. Between the respective bodies of the inner and outer tubes 401, 601 is defined a path 604 for conduction therethrough such as of saturated steam or hot water.

In this embodiment with such constitution as described, therefore, saturated steam for example, as it is generated at the boiler, is supplied through the superheater 2, where it becomes superheated steam, and enters via the rotary valve 3 into the heating tube 4, while the material is put on streams of the superheated steam, when the steam is passing the valve 3, and charged therewith into the tube 4 as a swirling stream generating tube adapted for heating as described. In the heating tube 4, the material is whirled to be well-mixed with and, concurrently, directly heated under pressure by the superheated steam, while, in addition thereto, being indirectly heated by the medium in the path 604. Then, through the restriction tube 5, the material as processed is discharged under atmospheric pressure.

FIG. 3 is a sectional view showing a partially modified example of the restriction tube 5 of the foregoing embodiment of the invention. Although in the embodiment the tube 5 is reduced at a longitudinally intermediate part of the tube body itself, in the modified example a restriction tube 502, which is uniform in inside diameter along the length, has fixed therein such a member 503 that is formed with an orifice 501' at the central part thereof.

Incidentally, in the embodiment of the present invention, the powder-like and/or granular substance as a material to be processed may be of an arbitrary kind or type: exemplarily, there can be enumerated grains, as primary products and as they are powdered or grained, chips such as of vegetables, materials of foods such as bread crumbs, starch powder, pepper and curry powder, medicines and medicine materials and fillers, feed and cosmetic materials, and the like.

Moreover, as the direct-heating medium to be supplied from the line 1 and mixed to be brought into direct contact with such material, when this is charged into the heating tube 4, there can be enumerated superheated steam, saturated steam, and the like, while superheated steam generally is preferred for its possible handling in a dry state.

In this respect, however, also saturated steam is quite effective for those materials of which fluidity is kept even when water is absorbed a little, exemplarily for grains such as soybean and wheat, and the like.

The condition of direct heating is controlled, in those processes intended for the sterilization of material, such that, while the temperature generally is desired to be relatively low for such intention, in the case of processing by saturated steam the pressure in terms of gauge pressure is kept at or under 5 kg/cm$^2$ and, preferably, set within a range of 0.5 to 2.5 kg/cm$^2$, and in the case of processing by superheated steam the pressure in terms of gauge pressure and the temperature are kept at or under 4 kg/cm$^2$ and at or below 300° C. respectively and, preferably, set within a range of 0.1 to 3 kg/cm$^2$ and at or below 250° C. respectively while having the material mixed to be held in direct contact with the superheated steam for a period within a range of 0.1 to 3 seconds.

On the other hand, in those processes intended for the denaturalization of material, such control is made of direct heating that, while the type of material to be processed is supposed to be limited particularly to grains for the simplicity of description, in the case of processing by saturated steam the pressure in terms of gauge pressure is kept within a range of 1 to 20 kg/cm$^2$ and, preferably, set within a range of 2 to 10 kg/cm$^2$, and in the case of processing by superheated steam the pressure in terms of gauge pressure and the temperature are kept within a range of 1 to 15 kg/cm$^2$ and at or below 350° C. respectively and, preferably, set within a range of 2 to 8 kg/cm$^2$ and at or below 300° C. respectively while having the material mixed to be held in direct contact with the superheated steam for a period within a range of 1 to 8 seconds.

Moreover, with respect to the condition of indirect heating, which is related mainly to the temperature of the indirect-heating medium and might well have effects on the product quality if this temperature be excessively high, such control is performed that, though depending on the type of material, the heating medium temperature preferably is kept at or below 300° C. for the sterilization purpose and at or below 350° C. for the denaturalization purpose. The indirect-heating medium may be saturated steam, superheated steam, hot gas, hot water, or the like, or there may be employed any of other suitable types of heater for indirect heating, such as an electric type heater.

Incidentally, according to the present invention, the necessary supply flow of a direct-heating medium is permitted to be minimized, so that a sufficient economy is expectable even in employment of what is called one-pass system, in which the direct-heating medium is to be wasted in a non-recycle manner and, hence, which has a good effect on the deodorization of materials to be processed.

Further, according to the present invention, it is permitted, like the case of the equipment 100 in the aforementioned embodiment, to utilize as a product discharge mechanism a nozzle as a restriction tube, while there may be utilized any of other suitable apparatuses such as a rotary valve. In this respect, in the case where a nozzle is employed as a product discharge mechanism, the pressure exerting on any material that is heated to be processed can be reduced to an atmospheric level in a shorter while, thus permitting a more effective swelling of the material, than the case of employment of a rotary valve.

Hereinbelow, a number of modifications of the aforementioned embodiment of the invention, as well as some modified examples of a part thereof, will be described one by one in line with the accompanying drawings. Like parts are designated by like reference numerals to thereby eliminate the redundancy of description.

Figure 4:
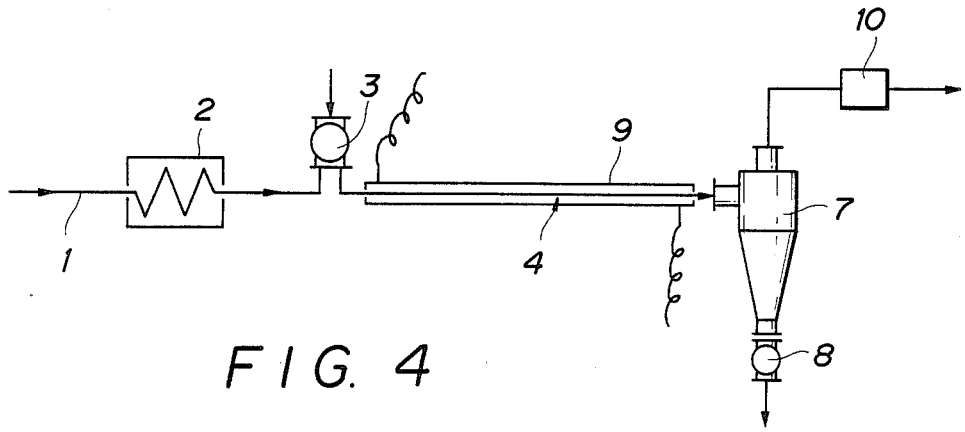
FIG. 4 is a schematic flow diagram of an equipment for processing by heating according to a first modification of the aforementioned embodiment of the invention, in which a direct-heating medium is let to run in a one-pass manner and there is employed as a product discharge mechanism a combination of a cyclone and a rotary valve.

In FIG. 4 is shown a first modification of the embodiment, which employs, as a product discharge mechanism, a combination of a cyclone 7 and a rotary valve 8 and, as an indirect-heating mechanism, an electric heater 9. The electric heater 9 is arranged around a heating tube 4 and adapted for heating the tube 4, from outside thereof, by conduction of electric current. According to this modification with the electric heater 9, a heating process equipment can be simplified in constitution. As the rotary valve 8, there may preferably be employed "a transfer device with a forced discharge apparatus" disclosed in Japanese Patent Publication No. 45-8927 (published on March 31, 1970) by the present applicant. Incidentally, designated at reference numeral 10 is a relief valve responsible for back pressure.

Figure 5:
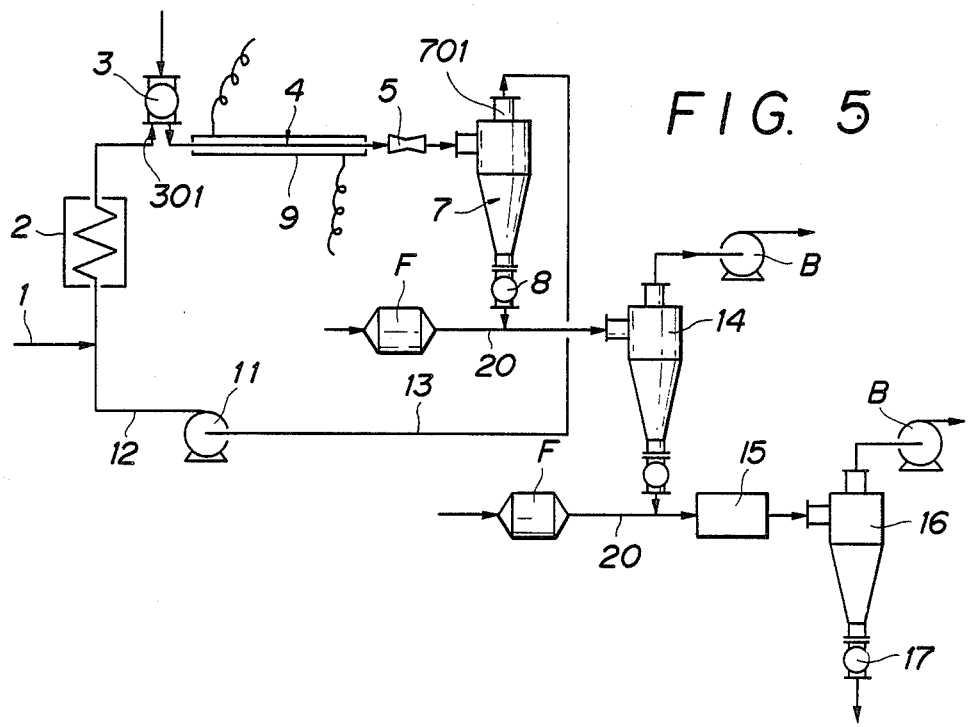
FIG. 5 is a schematic flow diagram of an equipment for processing by heating according to a second modification of the aforementioned embodiment of the invention, in which a direct-heating medium is let to run in a recirculating manner and there is employed as a product discharge mechanism a combination of a nozzle, a cyclone, and a rotary valve.

In FIG. 5 is shown a second modification of the embodiment, in which a direct-heating medium is recirculated through a recirculation circuit 12 with a compressor 11. A cyclone 7 communicating with a nozzle 5 has a medium outlet 701 thereof connected to the compressor 11, which in turn is connected to a medium inlet 301 of a rotary valve 3, thereby constituting the recirculation circuit 12. Of the circuit 12, a part 13 extending between from the nozzle 5 to the compressor 11 has a line pressure substantially equal to the atmospheric pressure.

The cyclone 7 is adapted to cooperate with a rotary valve 8 to separate a product from the direct-heating medium, which product is lead in an air transfer line 20 and transferred therealong to another cyclone 14, where it is deprived of residual direct-heating medium. Thereafter, the product is collected in a suitable manner such as through a cooler 15. In the modification shown in FIG. 7, such collection is effected by additional provision of combination of a cyclone 16 and a rotary valve 17. Incidentally, in FIG. 7, designated at reference character F is either of a pair of filters, and B is either of a pair of blowers.

Figure 6:
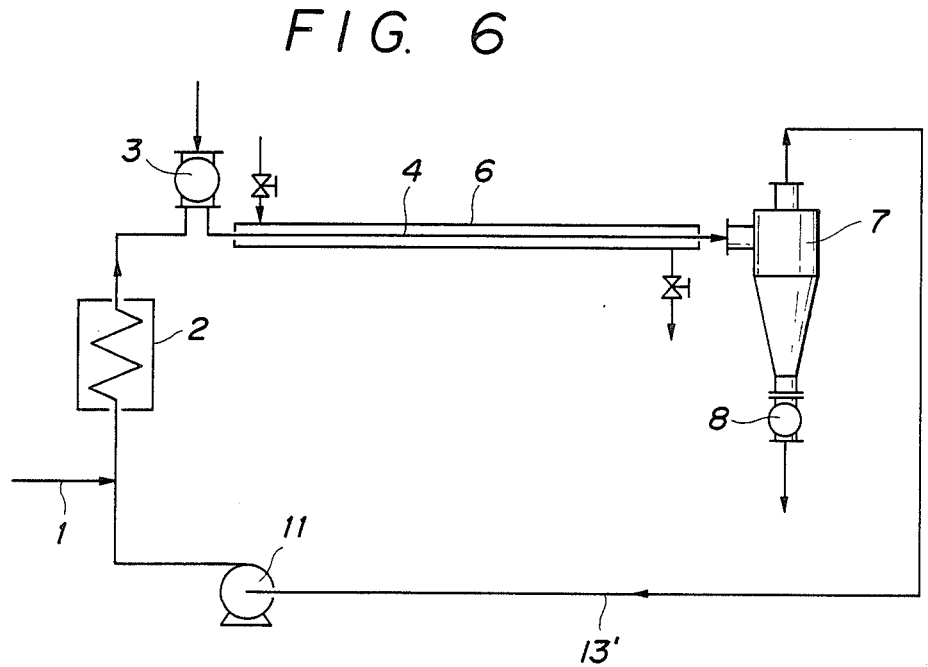
FIG. 6 is a schematic flow diagram of an equipment for processing by heating according to a third modification of the aforementioned embodiment of the invention, in which a direct-heating medium is let to run in a recirculating manner and there is employed as a product discharge mechanism a combination of a cyclone and a rotary valve.

In FIG. 6 is shown a third modification of the embodiment, in which also a direct-heating medium is recirculated through a recirculation circuit with a blower 11 and there is employed as a product discharge mechanism a combination of a cyclone 7 and a rotary valve 8, without using nozzles. The heating medium is returned from the cylone 7, through a return line 13', to the blower 11, so that the recirculation circuit is wholly put under pressure.

In FIGS. 7 to 10 are shown such modifications of the embodiment of the invention that a process stage by a heating tube is multiplied, as described below.

Figure 7:
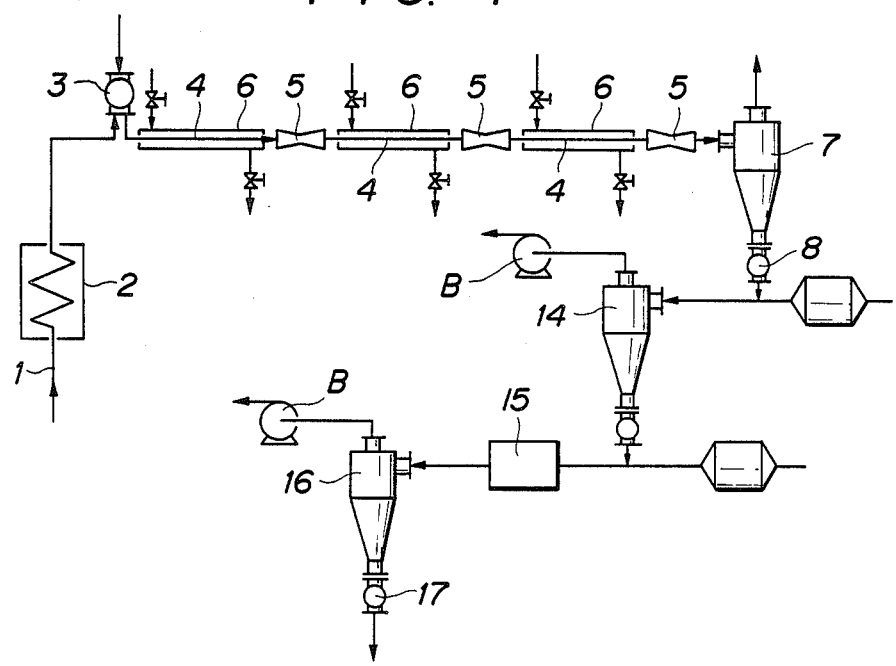
FIG. 7 is a schematic flow diagram of an equipment for processing by heating according to a fourth modification of the aforementioned embodiment of the invention, in which a process stage by a heating tube is multiplied, while having a direct-heating medium let to run in a one-pass manner, and there is employed as a product discharge mechanism a combination of a nozzle, a cyclone, and a rotary valve.

First, in FIG. 7 is shown a fourth modification of the embodiment, in which a process stage by a heating tube 4 is rendered triple, while using the same direct-heating medium, thus permitting the supply pressure of this medium to be raised. The heating tube 4 of each stage has downstream thereof a nozzle 5 connected in series thereto. A product from the nozzle 5 of the final stage is collected through a combination of a cyclone 7 and a rotary valve 8, another combination of a cyclone 14 and a rotary valve, a line including a cooler 15, and still another combination of a cyclone 16 and a rotary valve 17.

Figure 8:
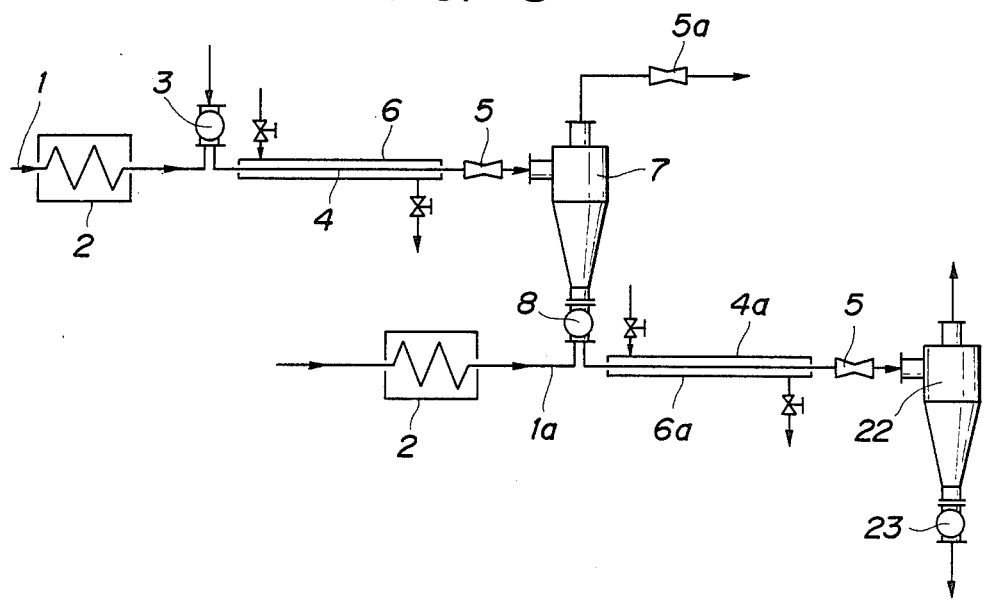
FIG. 8 is a schematic flow diagram of an equipment for processing by heating according to a fifth modification of the aforementioned embodiment of the invention, in which, at each of two stages as a double of a process stage by a heating tube, a direct-heating medium fed thereto from either of separate supply sources is let to run in a one-pass manner and there is employed as a product discharge mechanism a combination of a nozzle, a cyclone, and a rotary valve.

Next, in FIG. 8 is shown a fifth modification of the embodiment, in which a process stage by a heating tube is doubled to have primary and secondary stages and, at each stage thereof, a direct-heating medium is fed from either of separated direct-heating medium sources. A rotary valve 8, which is combined with a cyclone 7 installed downstream of the primary stage including a heating tube 4 fed with the heating medium from one of the medium sources, has let therein the direct-heating medium supplied from the other medium source through a line 1a, so that a powder-like and/or granular substance as once heated to be processed in the primary stage is further heated by a combination of a heating tube 4a and an indirect-heating mechanism 6a of the secondary stage, before collection of its product through a combination of a cyclone 22 and a rotary valve 23. According to this modification, the pressure and temperature of either stage, as well as the medium source thereof, can be set independendly of the other stage. Incidentally, in FIG. 8, designated at reference number 5a is a nozzle responsible for a back pressure.

Figure 9:
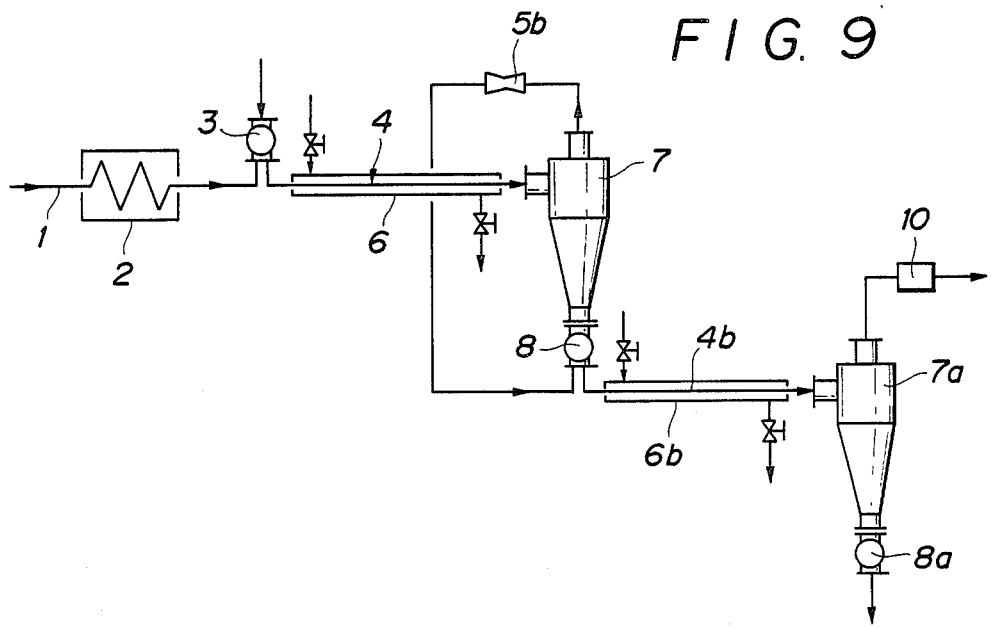
FIG. 9 is a schematic flow diagram of an equipment for processing by heating according to a sixth modification of the aforementioned embodiment of the invention, in which a process stage by a heating tube is doubled, with a direct-heating medium let to run in a one-pass manner as a whole and in a looped manner at a part, and there is employed as a product discharge mechanism a two-stage combination of a cyclone and a rotary valve.
Figure 10:
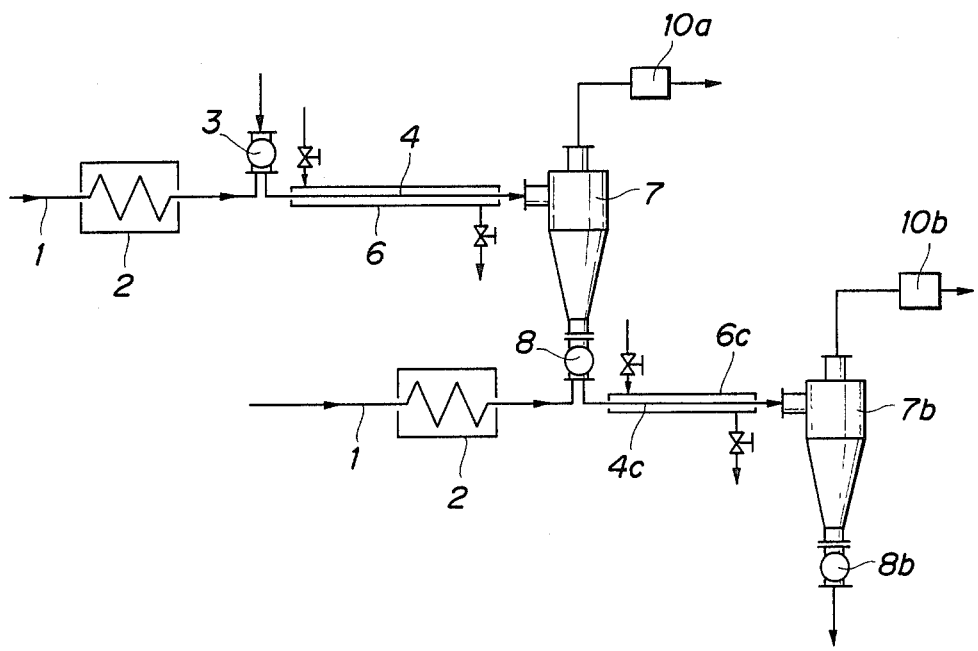
FIG. 10 is a schematic flow diagram of an equipment for processing by heating according to a seventh modification of the aforementioned embodiment of the invention, in which a process stage by a heating tube is doubled to be each respectively fed, in a one-pass manner, with a direct-heating medium from one of a pair of supply sources and there is employed as a product discharge mechanism a two-stage combination of a cyclone and a rotary valve.

Then, in FIGS. 9 and 10 are shown sixth and seventh modifications of the embodiment, each of which employs as a product discharge mechanism a combination of a cyclone and a rotary valve.

In the sixth modification shown in FIG. 9, a direct-heating medium supplied from a single direct-heating medium source is partially circulated to be returned, at the downstream end of a primary stage, through a nozzle 5b to a rotary valve 8, and a material heated to be processed in the primary stage is further heated by a combination of a heating tube 4b and an indirect-heating mechanism 6b of a secondary stage. Thereafter, a product is collected through a combination of a cyclone 7a and a rotary valve 8a.

In the seventh modification shown in FIG. 10, which has a pair of direct-heating medium sources separated to be independent from each other but differs from the fifth modification shown in FIG. 8 in that the seventh modification does not employ such nozzles as used in the fifth modification and instead thereof a pair of back-pressure responsible relief valves 10a, 10b are provided for a pair of cyclones 7, 7b of primary and secondary heating processes respectivety. A direct-heating medium supply line 1a of the secondary process is connected to a rotary valve 8 of the primary process, thereby permitting a processed material of the primary process to be further heated to be processed through a combination of a heating tube 4c and an indirect-heating mechanism 6c of the secondary process, before collection of its product to be discharged through a combination of the cyclone 7b and a rotary valve 8b.

In FIGS. 11 to 15 are shown a variety of modified examples of the restriction tube 5 as a nozzle, in each of which a restriction is adapted to have a variable effective cross-sectional area, as described below.

Figure 11:
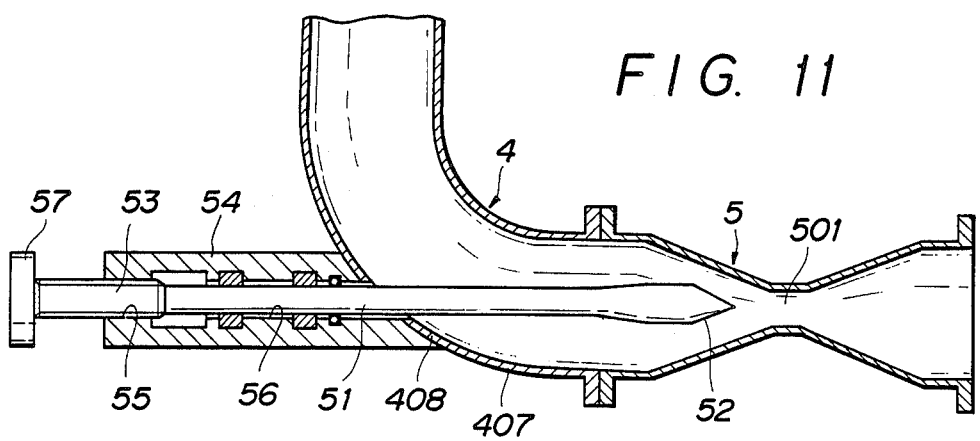
FIG. 11 is a view showing a second modified example of the aforementioned restriction tube, in which a tube is adapted to be variable of effective cross-sectional area.

First, in FIG. 11 is shown a second modified example, in which, while an outlet portion 407 of a heating tube 4 is curved like an inverse-L to have an enblow-like form, through a corner part 408 thereof a bar-like nozzle control rod 51 is inserted into a nozzle 5, the control rod 51 being adapted to be driven forward and back in the longitudinal direction of the nozzle 5. The nozzle control rod 51 has a distal end part 52 thereof adapted to be inserted into and extracted from the central part of a restriction 501 of the nozzle 5, the end part 52 being conically shaped to reduce the resistance to thereby make smooth the flow of a direct-heating medium. Moreover, the nozzle control rod 51 has at the proximal part thereof male threads 53 formed thereon and, on the other hand, a control rod holder 54, which is fixed to the corner part 408 of the heating tube 4 and hollowed in the form of a pipe, has at the proximal part thereof female threads 55 formed therein. By inserting the nozzle control rod 51 through a hollow 56 of the control rod holder 54, the male and the female threads 53, 55 are meshed with each other, thereby enabling the control rod 51 to be driven forward and back, while such forward or backward movement of the rod 51 is screw-adjusted by properly rotating a thumb 57 projected from the proximal end of the rod 51. In accordance with this screw adjustment, also the distal end part 52 of the rod 51 is forced to move forward and back to thereby adjust the effective cross-sectional area of the restriction 501.

Figure 12:
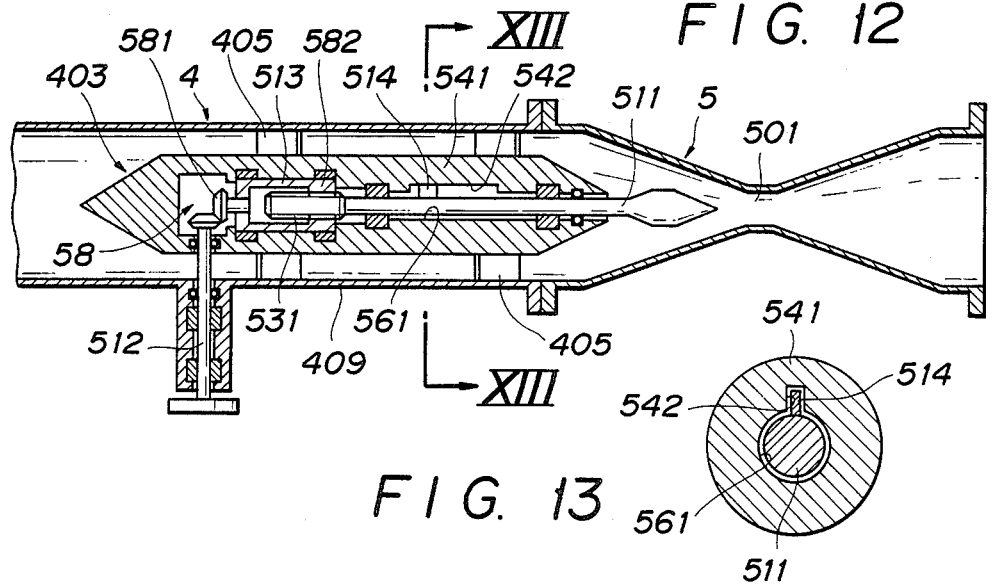
FIG. 12 is a view showing a third modified example of the aforementioned restriction tube, in which a tube is adapted to be variable of effective cross-sectional area.
Figure 13:
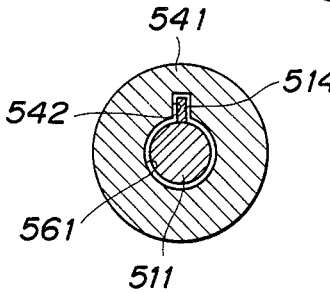
FIG. 13 shows a section along line XIII—XIII of FIG. 12.

Next, in FIG. 12 is shown a third modified example in which a nozzle cross-sectional-area varying mechanism is provided, while leaving an outlet portion 409 of a heating tube 4 as it is straight. In this modified example, a control rod holder 541 disposed in the heating tube 4 has inserted in a hollow 561 thereof a nozzle control rod 511 which is adapted to be driven forward and back by means of a pair of adjust rods 512, 513 engaged with each other through a bevel gear mechanism 58. More particularly, one gear 581 of the gear mechanism 58 has a cap nut-like holder 582 thereof screwed on a thread part 531 of the nozzle control rod 511, so that longitudinal movement of the control rod 511 is screw-adjustable, while, to prevent the control rod 511 from integrally rotating with the adjust rod 512, the control rod 511 has fixed thereon a key-like flat piece 514 engaged with a longitudinal groove 542 formed in the wall of hollow 561 of the control rod holder 541, as shown in FIG. 13. Incidentally, the control rod holder 541 is adapted to serve as a swirler 403, by providing there-around an adequte number of fins 405 for whirling streams of a direct-heating medium passing by.

Figure 14:
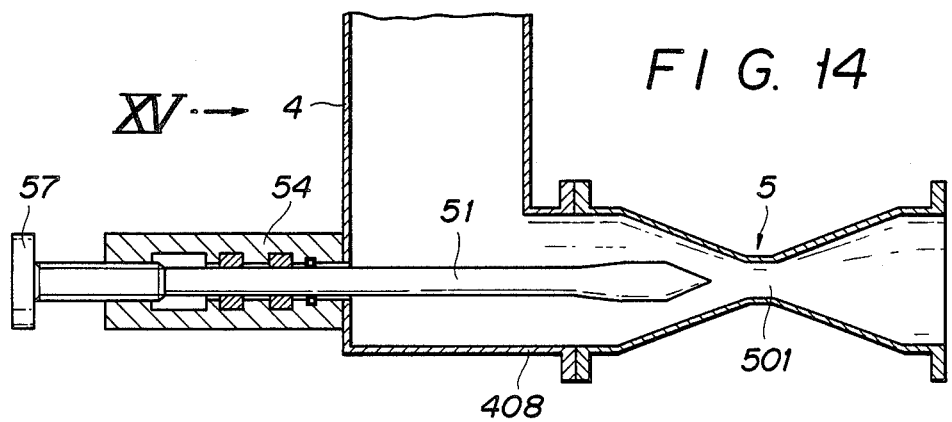
FIG. 14 is a view showing a fourth modified example of the aforementioned restriction tube, in which a tube is adapted to be variable of effective cross-sectional area.
Figure 15:
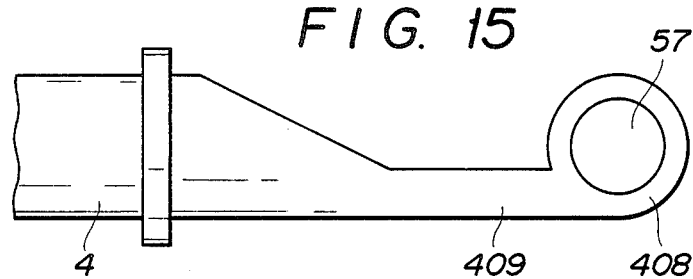
FIG. 15 shows an outline as a view in the direction of arrow XV of FIG. 14.

Then, shown in FIGS. 14 and 15 is a fourth modified example in which, while an outlet portion 408 of a heating tube 4 is bent at a right angle to be joined at the end thereof to a nozzle 5, through the bent part thereof a nozzle control rod 51 that is similar to the second modified example shown in FIG. 11 is inserted into the nozzle 5. Designated at reference numeral 54 is a control rod holder with a screw mechanism adapted for driving forward and back the control rod 51 to thereby render adjustable the cross-sectional area of a restriction 501 of the nozzle 5, while operation therefor is made by means of a thumb 57.

Incidentally, as shown in FIG. 15 as a view in the direction of arrow XV of FIG. 14, the heating tube 4 is narrowed in width at an access portion 409 thereof to the outlet portion 408, the access portion 409 being directed tangential to the outlet portion 408, thereby effectively swirling a direct-heating medium.

Figure 16:
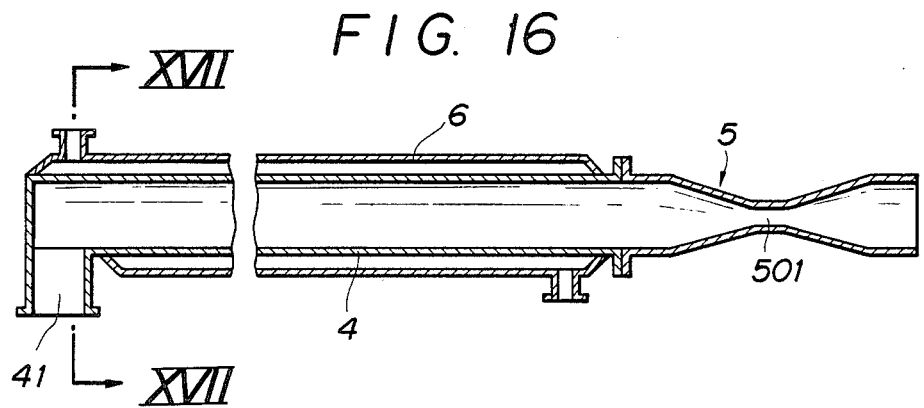
FIG. 16 is a view showing a modified example of a whirling stream generating mechanism in the aforementioned embodiment of the invention.
Figure 17:
FIG. 17 shows a section along line XVII—XVII of FIG. 16.

FIGS. 16 and 17 are sectional views for showing, as a modified example of the whirling stream generating mechanism of the aforementioned embodiment of the invention, an arrangement for effectively whirling a material as well as a direct-heating medium in a heating tube 4, in which as shown in FIG. 17 an inlet portion 41 of the heating tube 4 is directed tangential to the tube 4. It will be easily understood that material whirling streams can be intensified by combination of this modified example and the aforementioned swirler 403. Incidentally, in the example shown, there is employed an indirect-heating mechanism of a jacket type.

Figure 18:
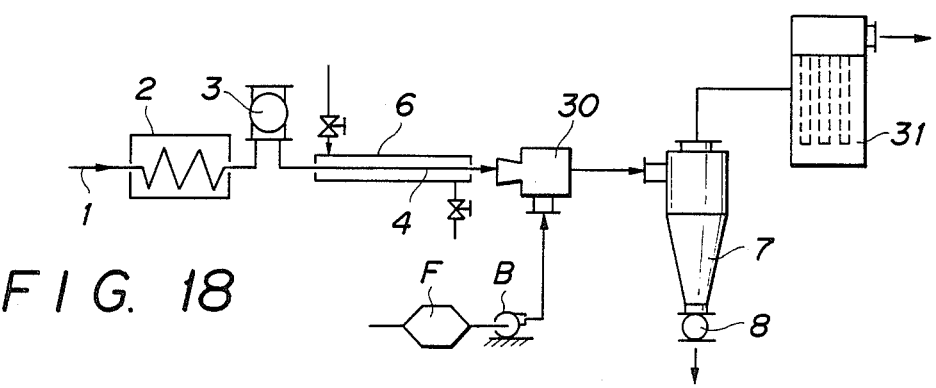
FIG. 18 is a schematic flow diagram of an equipment for processing by heating according to a eighth modification of the aforementioned embodiment of the invention, in which a direct-heating medium is let to run in a one-pass manner and there is employed as a product discharge mechanism a combination of a mixing nozzle, a cylcone, and a rotary valve.

Finally, in FIG. 18 is shown an eighth modification of the aforementioned embodiment of the invention, in which a mixing nozzle 30 is used as a product discharge mechanism. According to this modification, exemplarily in a case where superheated steam is employed as a direct-heating medium, the dew point of the direct-heating medium can be raised by adding air at the mixing nozzle 30, thereby permitting effective collection of fine dust at a bag filter 31 installed downstream of a product discharge point.

There will be given below a number of experimental examples for showing how the present invention is favorable in such nature of products as the rate of digestion, the degree of sterilization, the reduction of acid value, and the quantity of survived vitamins, by comparing a method for processing by heating according to the present invention with a conventional method according to Japanese Patent Publication No. 46-34747.

EXPERIMENTAL EXAMPLE 1

First, for a case in which de-fatted soybeans were heated to be processed, the results of an experiment is shown in Table 1 in the next page.

As will be comprehended from Table 1, according to the present invention, the heating time can be shortened, while obtaining a product having a good digestion rate.

TABLE 1

| | Denaturalization | |
|---|---|---|
| Items | Present* invention | Prior* art |
| Type of material | De-fatted soybean | De-fatted soybean |
| Charging rate, kg/hr | 300 | 4000 |
| Processing pressure, kg/cm$^2$G | 6.0 | 6.5 |
| Direct-heating medium, | Superheated steam | |
| Inlet temperature*, °C. | 220 | 195 |
| Outlet temperature*, °C. | 185 | 170 |
| Indirect-heating medium, | Electric heater | — |
| Wall temperature, °C. | 260 | — |
| Mixing ratio | 3.0 | 0.7 |
| Process time, sec. | 2.2 | 6.0 |
| Product analysis, | | |
| Digestion rate, % | 95.2 | 94.3 |
| Water content, | | |
| Before the process, wt % | 11.0 | 30.7 |
| After the process, wt % | 8.8 | 27.3 |

*Notes
(1) Present invention: The equipment shown in FIG. 1
(2) Prior art: Japanese Patent Publication No. 46-34747
(3) Inlet temperature: Temperature just before the contact with material
(4) Outlet temperature: Temperature just after the separation from material The rate of digestion was determined by applying an ordinary test procedure, in which: a denatured material (which may be wheat) as processed by heating is vacuum-dried at a low temperature and thereafter ground into powder; 1 g of this powder as sample is put in a shake test tube and, after having admixed with 10 ml of 0.5-M phosphate buffer solution (pH 7.2), 20 ml of an enzyme solution, and 1 ml of triol, the tube is sealed tight; the test tube is kept at 37° C. for seven days, while slowly shaking, to develop the disintegration of enzyme; then, distilled water is added to separated liquid to have a total volume of 100 ml, before centrifuging to separate into liquid and solid phases; and to 30 ml of the liquid-phase portion is then added 15 ml of 1.2-M trichloracetate and, after filtration of precipitates (non-dissolved proteins), 15 ml of filtrate is taken to measure the nitrogen content by Kjeldahl method. Further, in this procedure, by following like steps, there is separately run a blind test without adding the powder sample. Then, the digestion rate in terms of percent is computed by an expression, such that:

$$\text{digestion rate (\%)} = [(A-30)/B] \times 100,$$

where A equals to the nitrogen content in the main test minus that in the blind test, and B is the quantity of nitrogen contained in 1 g of the powder sample, of which measurement also is made by Kjeldahl method.

EXPERIMENTAL EXAMPLE 2

For a case in which buckwheat flour is heated to be processed, the results of an experiment are shown in Table 2.

As will be comprehended from Table 2, according to the present invention, the heating time can be shortened, while having a sterilization effect as good as the conventional method.

TABLE 2

| | Sterilization | |
|---|---|---|
| Items | Present* invention | Prior* art |
| Type of material | Buckwheat flour | Buckwheat flour |
| Charging rate, kg/hr | 120 | 150 |
| Processing pressure, kg/cm$^2$G | 2.0 | 2.5 |
| Direct-heating medium, | Superheated steam | |
| Inlet temperature*, °C. | 197 | 210 |
| Outlet temperature*, °C. | 180 | 185 |
| Indirect-heating medium, | Electric heater | — |
| Wall temperature, °C. | 230 | — |
| Mixing ratio | 2.0 | 0.6 |
| Process time, sec. | 0.8 | 5.0 |
| Number of alive germs, | | |
| Before the process, per g | $5.0 \times 10^5$ | $5.5 \times 10^5$ |
| After the process, per g | 0 | 0 |

*Notes
(1) Present invention: The equipment shown in FIG. 1
(2) Prior art: Japanese Patent Publication No. 46-34747
(3) Inlet temperature: Temperature just before the contact with material
(4) Outlet temperature: Temperature just after the separation from material

EXPERIMENTAL EXAMPLE 3

For a case in which rice bran is heated to be processed, the results of an experiment are shown in Table 3.

As will be comprehended from Table 3, according to the present invention, the acid value of product can be reduced without reducing the lipid of material.

Incidentally, the acid value was determined by an ordinary measurement method.

For the same case as above, also the vitamin content of product was measured. The results of this measurement are shown in Table 4.

As will be comprehended from Table 4, according to the present invention, various heating processes such as for sterilization can be executed, without decreasing the amount of vitamins present in the material.

Incidentally, for the measurement of vitamins, the following methods were employed:

Vitamin Measurement Methods

1. Vitamin $B_1$: Thiochrome fluorescence method
2. Vitamin $B_2$: Lumi-flavin fluorescence method
3. Vitamin $B_6$: Microbiological measurement method
4. Vitamin E: Liquid chromatography
5. Niacin: Microbiological quantitation method

TABLE 3

| Items | Present* invention | Prior* art |
|---|---|---|
| Type of material | Rice bran | Rice bran |
| Charging rate, kg/hr | 100 | 100 |
| Processing pressure, kg/cm$^2$G | 2.0 | 2.0 |
| Direct-heating medium, | Superheated steam | |
| Inlet temperature*, °C. | 195 | 220 |
| Outlet temperature*, °C. | 175 | 180 |
| Indirect-heating medium, | Electric heater | — |
| Wall temperature, °C. | 230 | — |

TABLE 3-continued

| Items | Present* invention | Prior* art |
|---|---|---|
| Mixing ratio | 1.6 | 0.42 |
| Process time, sec. | 1.0 | 5.2 |
| Product analysis, | | |
| Acid value, | | |
| Before the process, | 22.0 | 22.0 |
| After the process, | 10.5 | 15.3 |
| Lipid, | | |
| Before the process, | 24.1 | 24.0 |
| After the process, | 23.3 | 23.8 |

*Notes
(1) Present invention: The equipment shown in FIG. 1
(2) Prior art: Japanese Patent Publication No. 46-34747
(3) Inlet temperature: Temperature just before the contact with material
(4) Outlet temperature: Temperature just after the separation from material

TABLE 4

| Vitamins in mg % | Vitamin content of material | Survived quantity by process according to present invention | Survived quantity by process according to prior art |
|---|---|---|---|
| Vitamin $B_1$ | 2.50 | 2.30 | 1.85 |
| Vitamin $B_2$ | 0.50 | 0.40 | 0.27 |
| Vitamin $B_6$ | 4.5 | 4.0 | 3.2 |
| Vitamin E | 15.1 | 14.3 | 13.0 |
| Niacin | 48.0 | 46.8 | 46.1 |

As will be understood from the foregoing description, according to the present invention, which is of such a system that in comparison with conventional art the flow rate of a direct-heating medium is decreased by combination of direct heating and indirect heating, individual equipments such as a heating tube and a cyclone can be small-sized. In addition to that, sufficient economy is expectable even when following what is called one-pass system in which a direct-heating medium is wasted.

Moreover, it also is possible to shorten the heating time, thus permitting useful ingredients in various materials, such as vitamins for example, to survive in a sufficient proportion even when such material is processed by heating.

Further, also in the case of those materials containing lipids, the acid value can be decreased, while leaving a notable proportion of the lipids as they are.

Hereinbelow, there will be given a number of process examples performed by use of a heating process equipment according to the present invention.

First, description will be made of process examples 1 to 4 intended for sterilization. The heating process equipment employed was as shown in FIG. 1 (hereinbelow also, like parts are referenced by like reference numerals), and there was a single heating stage consisting of a heating tube 4 of a 60-mm inside diameter and a 6-m length. Thirty swirlers 403 were arranged at intervals of 20 cm. As a product discharge mechanism, there was employed a nozzle 5 of the type shown in FIG. 2, which was 9.5 mm in inside diameter. Further, as an indirect-heating implement, an electric heater of a 10 kW rating was provided by uniformly coiling a heating element thereof on the heating tube 4.

PROCESS EXAMPLE 1

Raw rice bran as material, 12 mesh or smaller in grain size and 12.0 wt % in water content, was charged at a rate of 100 kg/hr into the heating tube 4, through which superheated steam 2 kg/cm$^2$G and 194° C. was being conducted. With surface temeprature at the outside of wall of the heating tube 4 held at 240° C. in average, the material was heated, while whirling, in the tube 4 for approximately 0.7 seconds, before discharging under atmospheric pressure. At the stage of discharge, the temperature of superheated steam was 173° C. at the outlet of the heating tube 4, while the consumption of superheated steam was 60 kg/hr.

The number of alive germs per gram, which was $4.2 \times 10^6$ before the heating process, became 6 after the process, and also the water content was decreased to 5.2 wt %.

PROCESS EXAMPLE 2

Adlay as material, fully granular and of a 7.5-wt % water content, was charged as material at a rate of 130 kg/hr into the heating tube 4, through which superheated steam 2 kg/cm$^2$G and 200° C. was being conducted. With surface temeprature at the outside of wall of the heating tube 4 held at 250° C. in average, the material was heated, while whirling, in the tube 4 for approximately 0.8 seconds, before discharging under atmospheric pressure. At the stage of discharge, the temperature of superheated steam was 160° C. at the outlet of the heating tube 4, while the consumption of superheated steam was 70 kg/hr.

The number of alive germs per gram, which was $8.1 \times 10^5$ before the heating process, became 20 after the process, and also the water content was decreased to 6.0 wt %.

PROCESS EXAMPLE 3

Rice chaff as material, 10 mesh or smaller in grain size and 13.0 wt % in water content, was charged at a rate of 150 kg/hr into the heating tube 4, through which superheated steam 2 kg/cm$^2$G and 200° C. was being conducted. With surface temperature at the outside of wall of the heating tube 4 held at 245° C. in average, the material was heated, while whirling, in the tube 4 for approximately 0.8 seconds, before discharging under atmospheric pressure. At the stage of discharge, the temperature of superheated steam was 160° C. at the outlet of the heating tube 4, while the consumption of superheated steam was 65 kg/hr.

The number of alive germs per gram, which was $5.0 \times 10^6$ before the heating process, became $6 \times 10$ after the process, and also the water content was decreased to 3.5 wt %.

PROCESS EXAMPLE 4

Marine alga as material, 150 mesh or smaller in grain size and 12.5 wt % in water content, was charged at a rate of 120 kg/hr into the heating tube 4, through which superheated steam 2.0 kg/cm$^2$G and 200° C. was being conducted. With surface temeprature at the outside of wall of the heating tube 4 held at 250° C. in average, the material was heated, while whirling, in the tube 4 for approximately 0.8 seconds, before discharging under atmospheric pressure. At the stage of discharge, the temperature of superheated steam was 175° C. at the outlet of the heating tube 4, while the consumption of superheated steam was 70 kg/hr.

The number of alive germs per gram, which was $5.3 \times 10^3$ before the heating process, became 20 after the process, and also the water content was decreased to 9 wt %.

Next, description will be made of process examples 5 to 8 intended for denaturalization. The heating process equipment employed was as shown in FIG. 7 (hereinbelow as well, like parts are referenced by like reference numerals), and a heating stage consisting of a heating tube 4 of a 60-mm inside diameter and a 6-m length was rendered triple, while having a direct-heating medium let to run in a one-pass manner. Ninety swirlers 43 were arranged at intervals of 20 cm. To constitute a three-staged product discharge mechanism, there were employed nozzles 5 of the type shown in FIG. 2, of which inside diameter was 7.0 mm at a first stage, 10.0 mm at a second stage, and 14.5 mm at a third stage. Further, as an indirect-heating implement of each heating stage, an electric heater of a 10 kW rating was provided by uniformly coiling a heating element thereof on the heating tube 4.

PROCESS EXAMPLE 5

De-fatted soybeans as material, 16 to 243 mesh in grain size and 11.0 wt % in water content, were charged at a rate of 300 kg/hr into the heating tube 4 of first heating stage, through which superheated steam was being conducted as the direct-heating medium. Then, the material was heated to be processed, at the heating tube 4 of second heating stage and in turn at that of third heating stage, before discharging under atmospheric pressure. There resulted a product of a 95-% digestion rate and a 7.5-wt % water content.

Of superheated steam, the temperatures at the inlet and the outlet of the heating tube 4 and the pressure therein were 220° C., 200° C. and 6.0 kg/cm$^2$G at the first heating stage, 200° C., 190° C. and 3.4 kg/cm$^2$G at the second heating stage, and 190° C., 185° C. and 1.8 kg/cm$^2$G at the third heating stage, respectively, while the steam consumption was 100 kg/hr and the heating time was approximately 2 seconds.

PROCESS EXAMPLE 6

Crushed wheat as material, 12 to 60 mesh in grain size and 12.1 wt % in water content, were charged at a rate of 250 kg/hr into the heating tube 4 of first heating stage, through which superheated steam was being conducted as the direct-heating medium. Then, the material was heated to be processed, at the heating tube 4 of second heating stage and in turn at that of third heating stage, before discharging under atmospheric pressure. There was resulted a product of a digestion rate of 94.3 %, a conversion of 73.0 % to α-starch, and a water content of 8 wt %.

Incidentally, the conversion in terms of % to α-starch was determined in the following way: 0.5 g of the sample as finely ground was accurately weighed out, then dispersed in 40 ml of water, admixed with 20 ml of 2-N acetate buffer (pH 4.8), and left standing at 37° C. To the mixture was then added 5 ml of an enzyme solution prepared by dissolving 0.6 g of an Endomyces, enzyme (saccharogenic amylase) (Matsurase M-00; Matsutani Kagaku Co.) in 250 ml of 0.008-M acetate buffer. The mixture was allowed to react for one hour and the reaction was terminated with 4 ml of 2-N sodium hydroxide solution. The reaction mixture was made up to 100 ml with water, filtered through Toyo filter paper No. 5A, and the filtrate was assayed for reducing sugar by the SOMOGYI method. The control experiment was run by by accurately weighing out 0.5 g of the same sample, dispersing the sample in 40 ml of water, admixing with 5 ml of 2-N sodium hydroxide solution to effect complete conversion (100%) to α-starch, neutralizing the converted solution, allowing the neutralized solution to react with the same enzyme solution as used above, and assaying the reaction mixture for reducing sugar. The percentage conversion to α-starch was calculated by the following equation:

Conversion (%) to α-starch = [(reducing sugar in sample)/(reducing sugar in the control)] × 100.

Of superheated steam, the temperatures at the inlet and the outlet of the heating tube 4 and the pressure therein were 250° C., 210° C. and 6.0 kg/cm$^2$G at the first heating stage, 210° C, 190° C. and 3.3 kg/cm$^2$G at the second heating stage, and 190° C., 180° C. and 1.8 kg/cm$^2$G at the third heating stage, respectively, while the steam consumption was 100 kg/hr and the heating time was approximately 2 seconds.

PROCESS EXAMPLE 7

Polished rice as material, fully granular and of a 13.0-wt % water content, were charged at a rate of 300 kg/hr into the heating tube 4 of first heating stage, through which superheated steam was being conducted as the directheating medium. Then, the material was heated to be processed, at the heating tube 4 of the second heating stage and in turn at that of the third heating stage, before discharging under atmospheric pressure. There resulted a product of a conversion of 90 % to α-starch and a water content of 8.5 wt %.

Of superheated steam, the temperatures at the inlet and the outlet of the heating tube 4 and the pressure therein were 220° C., 200° C. and 4.0 kg/cm$^2$G at the first heating stage, 200° C., 180° C. and 2.7 kg/cm$^2$G at the second heating stage, and 180° C., 170° C. and 1.5 kg/cm$^2$G at the third heating stage, respectively, while the steam consumption was 80 kg/hr and the heating time was approximately 2 seconds.

PROCESS EXAMPLE 8

Ground corn as material, 6 to 42 mesh in grain size and 10.5 wt % in water content, were charged at a rate of 250 kg/hr into the heating tube 4 of the first heating stage, through which superheated steam was being conducted as the direct-heating medium. Then, the material was heated to be processed, at the heating tube 4 of the second heating stage and in turn at that of the third heating stage, before discharging under atmospheric pressure. There resulted a product of a conversion of 75 % to α-starch, and a water content of 9.5 wt %.

Of superheated steam, the temperatures at the inlet and the outlet of the heating tube 4 and the pressure therein were 250° C., 220° C. and 6.0 kg/cm$^2$G at the first heating stage, 220° C., 190° C. and 4.0 kg/cm$^2$G at the second heating stage, and 190° C., 175° C. and 2.8 kg/cm$^2$G at the third heating stage, respectively, while the steam consumption was 100 kg/hr and the heating time was approximately 2 seconds.

Although there has been described what is at present considered to be the preferred embodiment of the invention, it will be understood that the present invention may be embodied in other specific forms without departing from the spirit or essential characteristics thereof. The present embodiment is therefore to be considered in all respects as illustrative and not restrictive. The scope of the invention is indicated by the appended claims rather than by the foregoing description.

We claim:

1. A method for processing by heating a powder-like and or granular substance, comprising:
    charging said powder-like and/or granular substance as a matter to be processed into a heated and pressurized medium stream adapted for directly heating;
    heating said powder-like and/or granular substance while transferring said powder-like and/or granular substance in a heating tube (4, 6, 9) by said direct-heating medium stream;
    discharging from said heating tube said powder-like and/or granular substance as it is heated to be processed by said direct-heating medium stream;
    selectively varying the pressure of the medium stream within the tube by selectively restricting the discharge of the medium stream from the tube; and
    whirling said direct-heating medium stream in said heating tube (4) to spirally transfer said powder-like and/or granular substance.

2. A method for processing by heating according to claim 1, further comprising:
    means (6, 9) for indirectly heating said powder-like and/or granular substance by heating said heating tube (4).

3. A method for processing by heating according to claim 2, wherein:
    said indirect-heating means (6) comprises an additional heating medium stream arranged on the outside of said heating tube (4).

4. A method for processing by heating according to claim 2, wherein:
    said indirect-heating means (9) comprises electric heater means (9) disposed on the outside of said heating tube (4).

5. A method for processing by heating according to claim 1, wherein:
    said direct-heating medium stream comprises superheated steam.

6. A method for processing by heating according to claim 1, wherein:
    said heating to process is adapted for a denaturalization process of said powder-like and/or granular substance.

7. A method for processing by heating according to claim 1, wherein:
    said heating to process is adapted for a sterilization process of said powder-like and/or granular substance.

8. A method for processing by heating a powder-like and/or granular substance, comprising:
    a step of charging said powder-like and/or granular substance as a matter to be processed into a heated and pressurized medium stream adapted for directly heating;
    a step of heating to process while transferring said powder-like and/or granular substance in a heating tube (4, 6, 9) by said direct-heating medium stream;
    a step of indirectly heating said powder-like and/or granular substance by heating said heating tube (4); and
    a step of discharging from said heating tube (4, 6, 9), through discharging means (5), said powder-like and/or granular substance as it is heated to be processed by said direct-heating medium stream, wherein:
    said direct-heating medium stream is made to whirl to spirally transfer said powder-like and/or granular substance in said heating tube (4), and said discharging means (5) is adapted to control the pressure in said heating tube (4).

9. A method for processing according to claim 8, further comprising the step of controlling the pressure of the medium stream within the heating tube by controlling the discharge means to selectively vary a medium stream flow area at the discharge means.

10. A method for processing by heating according to claim 8, wherein:
    said heating tube (4) and said discharging means (5) are provided plural in number, respectively. (FIGS. 7, 8)

11. A method for processing by heating according to claim 8, wherein:
    said discharging means (5) comprises nozzle means (5).

12. A method for processing by heating according to claim 11, wherein:
    said nozzle means (5) includes means for varying the cross-sectional area of the restriction means. (FIGS. 11, 12, 14).

13. An equipment for processing by heating, comprising:
    a heating tube (4);
    means (3) for charging a powder-like and/or granular substance as a matter to be processed into said heating tube (4);
    heating medium stream supply means (1, 2, 11) for supplying a medium stram adapted for directly heating said powder-like and/or granular substance and for transferring said powder-like and/or granular substance in said heating tube (4);
    means (6, 9) for indirectly heating said powder-like and/or granular substance by heating said heating tube (4);
    whirling stream generation means (403, 41) for making said medium stream whirl to spirally transfer said powder-like and/or granular substance in said heating tube (4), discharging means (5) for discharging from said heating tube (4) said powder-like and/or granular substance as it is heated to be processed by said medium stream; and
    said discharging means (5) being adapted to control the pressure in said heating tube (4).

14. An equipment for processing by heating according to claim 13, wherein:
    said indirect-heating means (6) comprises a jaket (6) adapted to provided an additional heating medium on the outside of said heating tube (4).

15. An equipment for processing by heating according to claim 13, wherein:
    said indirect-heating means (9) comprises electric heater means (9) disposed on the outside of said heating tube (4).

16. An equipment for processing by heating according to claim 13, wherein:
    said discharging means (5) comprises nozzle means (5).

17. An equipment for processing for processing by heating according to claim 16, wherein:
    said nozzle means (5) has a variable effective cross-sectional area. (FIGS. 11, 12, 14).

* * * * *

UNITED STATES PATENT AND TRADEMARK OFFICE
CERTIFICATE OF CORRECTION

PATENT NO. : 4,709,487
DATED : December 1, 1987
INVENTOR(S) : Takeshi Akao, Toshio Furukawa It is certified that error appears in the above-identified patent and that said Letters Patent are hereby corrected as shown below:

Column 14, line 1, "temeprature" should be --temperature--.

Column 15, line 66, "by by accurately" should read --by accurately--.

Column 18, line 34, "stram" should read --stream--.

Column 18, line 52, "jaket" should read --jacket--.

Signed and Sealed this

Thirty-first Day of May, 1988

Attest:

DONALD J. QUIGG

*Attesting Officer*　　　　*Commissioner of Patents and Trademarks*